US012186281B2

(12) United States Patent
Shah et al.

(10) Patent No.: US 12,186,281 B2
(45) Date of Patent: *Jan. 7, 2025

(54) ORAL SOLID CANNABINOID OIL COMPOSITION FOR TREATING GASTROINTESTINAL DISORDERS

(71) Applicant: SOCIETE DES PRODUITS NESTLE S.A., Vevey (CH)

(72) Inventors: Syed M. Shah, Boca Raton, FL (US); Fred Hassan, Boca Raton, FL (US)

(73) Assignee: Societe des Produits Nestle S.A., Vevey (CH)

( * ) Notice: Subject to any disclaimer, the term of this patent is extended or adjusted under 35 U.S.C. 154(b) by 154 days.

This patent is subject to a terminal disclaimer.

(21) Appl. No.: 17/758,315

(22) PCT Filed: Jan. 8, 2021

(86) PCT No.: PCT/EP2021/050245
§ 371 (c)(1),
(2) Date: Jul. 1, 2022

(87) PCT Pub. No.: WO2021/140183
PCT Pub. Date: Jul. 15, 2021

(65) Prior Publication Data
US 2023/0065736 A1     Mar. 2, 2023

Related U.S. Application Data

(60) Provisional application No. 62/958,392, filed on Jan. 8, 2020.

(51) Int. Cl.
*A61K 31/05* (2006.01)
*A61K 9/16* (2006.01)
*A61K 9/50* (2006.01)

(52) U.S. Cl.
CPC ............ *A61K 31/05* (2013.01); *A61K 9/1652* (2013.01); *A61K 9/1694* (2013.01); *A61K 9/5073* (2013.01)

(58) Field of Classification Search
None
See application file for complete search history.

(56) References Cited

U.S. PATENT DOCUMENTS

| 2014/0017325 A1 | 1/2014 | Shah et al. |
| 2018/0078504 A1 | 3/2018 | Sacks et al. |
| 2018/0085308 A1 | 3/2018 | Renwick et al. |

FOREIGN PATENT DOCUMENTS

| CN | 103796637 A | 5/2014 |
| CN | 108853079 A | 11/2018 |

(Continued)

OTHER PUBLICATIONS

Anonymous "Pharma Grade CBD Wellness Capsules—Hempcine—Buy CBD Oils, CBD Capsules, CBD Creams, CBD Gummies, CBD Bath Bombs—100% Natural Hemp CBD—Pharma Grade CBD—Hempcine" Dec. 31, 2019, retrieved from the Internet: https://www.hempcine.com/product/hemp-cbd-capsule/3, 3 pages.

(Continued)

*Primary Examiner* — Kyung S Chang
(74) *Attorney, Agent, or Firm* — K&L Gates LLP

(57) ABSTRACT

Cannabinoid oil compositions may be used to treat gastrointestinal disorders. An example of the composition is an oral multiparticulate dosage form including a plurality of individual particulates including a solid core with an effective amount of cannabinoid oil bound in microcrystalline cellulose therein and an enteric coating over the solid core.

17 Claims, 2 Drawing Sheets

(56) References Cited

FOREIGN PATENT DOCUMENTS

| CN | 109789095 A | 5/2019 |
|---|---|---|
| WO | 2017193072 A1 | 11/2017 |
| WO | 2018071581 | 4/2018 |
| WO | 2019082171 | 5/2019 |
| WO | 2019234743 | 12/2019 |

OTHER PUBLICATIONS

Ri-Lu et al., "Research Progresses in Pathogenesis, Diagnosis, and Treatment of Diabetic Gastroparesis", Journal of Shanghai Jiao Tong University (Medical Science), vol. 36, Issue No. 5, May 31, 2016, pp. 761-766.

Office Action Received for Application No. CN202180007577.3, mailed on Dec. 22, 2023, 9 Pages (Official Copy Only).

ORAL SOLID CANNABINOID OIL COMPOSITION FOR TREATING GASTROINTESTINAL DISORDERS

CROSS REFERENCE TO RELATED APPLICATIONS

The present application is a National Stage of International Application No. PCT/EP2021/050245, filed on Jan. 8, 2021, which claims priority to U.S. Provisional Patent Application No. 62/958,392, filed on Jan. 8, 2020, the entire contents of which are being incorporated herein by reference.

FIELD

This relates to the field of cannabinoid oil formulations and, more particularly, to cannabinoid oil formulations for treating gastrointestinal disorders.

BACKGROUND

Cannabinoids are a class of compounds that act on cannabinoid receptors in the body. Cannabinoid receptors are part of the body's endocannabinoid system, which is composed of the cannabinoid receptors, endogenous cannabinoids called endocannabinoids, and chemicals used to synthesize endocannabinoids. Endocannabinoids are neurotransmitters.

Cannabinoids have been studied for decades for their therapeutic effects and some have been approved as drugs. EPIDIOLEX® is an oral solution containing cannabidiol "CBD" for treating certain forms of epilepsy. SATIVEX® is an aerosol spray containing CBD and tetrahydrocannabinol "THC" for treating pain in patients with multiple sclerosis. MARINOL®, which contains a synthetic form of THC called dronabinol, is used to treat emesis associated with chemotherapy and AIDS-related anorexia related to weight loss.

Others have reported that cannabinoids may be used to treat gastrointestinal disorder symptoms because cannabinoid receptors CB1 and CB2 are located in the gastrointestinal tract. According to Gyires and Zádori in "Role of Cannabinoids in Gastrointestinal Mucosal Defense and Inflammation," *Current Neuropharmacology*, Vol. 14, pgs. 935-951 (2016), there are numerous studies reporting therapeutic benefits of cannabinoids against inflammatory bowel diseases, including Crohn's disease and ulcerative colitis, for example.

BRIEF SUMMARY

The problem with treating gastrointestinal disorders using cannabinoids is that there is a shortage of oral cannabinoid dosage forms that can specifically target areas of inflammation in the gastrointestinal tract and can bypass CB2 receptors in the stomach. This problem is solved using an oral pharmaceutical dosage form comprising a solid matrix of microcrystalline cellulose and a cannabinoid oil.

An example of such a composition includes an oral multiparticulate dosage form including a plurality of individual particulates. The individual particulates have a solid core including an effective amount of cannabinoid oil bound in microcrystalline cellulose and an enteric coating over the solid core. The composition may further include one or more of the following additional features.

The individual particulates may be spheroidal, have an average diameter of 0.5 mm to 1.7 mm, and further include an enteric coating material and a disintegrant combination that cause the individual particulates to release most of the cannabinoid oil in a subject's duodenum for treating inflammation of the duodenum.

The individual particulates may be spheroidal, have an average diameter of 0.5 to 1.7 mm, and may be configured to release most of the cannabinoid oil in the jejunum for treating inflammation of the jejunum.

The individual particulates may be spheroidal, have an average diameter of 0.5 to 1.7 mm, and may be configured to release most of the cannabinoid oil in the ileum for treating inflammation of the ileum.

The individual particulates may be spheroidal, have an average diameter of 1.8 to 3 mm, and the dosage form may be configured to release the cannabinoid oil for at least 6 hours throughout the intestines.

The cannabinoid oil may be bound in microcrystalline cellulose by being stored within microcrystalline cellulose's fibrous network.

The cannabinoid oil bound in microcrystalline cellulose may be substantially dry.

A ratio of the cannabinoid oil to MCC may be 0.5:1 to 1.5:1.

The individual particulates may further include 10% w/w to 50% w/w cannabinoid oil, 40% w/w to 75% w/w microcrystalline cellulose, 2% w/w to 10% w/w methyl cellulose, and 2% w/w to 35% w/w enteric coating.

The cannabinoid oil may include CBD oil.

The composition may include any combination of these features.

An example of a processing method includes wet granulating microcrystalline cellulose and a cannabinoid oil together forming a solid matrix in which the cannabinoid oil is bound in the MCC and combining the solid matrix with at least one pharmaceutical excipient to form an oral pharmaceutical dosage form. The method may further include one or more of the following additional features.

Wet granulating may be performed in a high shear mixer above room temperature for 10 minutes to 20 minutes.

The oral pharmaceutical dosage form may be a multiparticulate dosage form including a plurality of individual spheroidal particulates having an average diameter of 0.5 mm to 3 mm.

The cannabinoid oil may be bound in microcrystalline cellulose by being stored within microcrystalline cellulose's fibrous network.

The cannabinoid oil bound in microcrystalline cellulose may be substantially dry.

A ratio of the cannabinoid oil to MCC may be 0.5:1 to 1.5:1.

The oral pharmaceutical dosage form may include 10% w/w to 50% w/w cannabinoid oil, 40% w/w to 75% w/w microcrystalline cellulose, 2% w/w to 10% w/w methyl cellulose, and 2% w/w to 35% w/w enteric coating.

The cannabinoid oil may include CBD oil.

The method may further include any combination of the these features.

An example of a therapeutic method includes treating a gastrointestinal disorder by administering an effective amount of the composition above to a subject having a gastrointestinal disorder. The method may further include one or more of the following additional features.

The individual particulates may be spheroidal, have an average diameter of 0.5 mm to 1.7 mm, and further comprise an enteric coating material and a disintegrant combination that cause the individual particulates to release most of the cannabinoid oil in a subject's duodenum for treating gastroparesis and/or functional dyspepsia.

The individual particulates may be spheroidal, have an average diameter of 0.5 to 1.7 mm, and may be configured to release most of the cannabinoid oil in the jejunum for treating inflammatory bowel syndrome.

The individual particulates may be spheroidal, have an average diameter of 0.5 to 1.7 mm, and may be configured to release most of the cannabinoid oil in the ileum for treating Crohn's disease, ileitis, and/or ulcerative colitis.

The individual particulates may be spheroidal, have an average diameter of 1.8 to 3 mm, and the dosage form may be configured to release the cannabinoid oil for at least 6 hours throughout the intestines.

The cannabinoid oil may be bound in microcrystalline cellulose by being stored within microcrystalline cellulose's fibrous network.

The cannabinoid oil bound in microcrystalline cellulose may be substantially dry.

A ratio of the cannabinoid oil to MCC may be 0.5:1 to 1.5:1.

The individual particulates may further include 10% w/w to 50% w/w cannabinoid oil, 40% w/w to 75% w/w microcrystalline cellulose, 2% w/w to 10% w/w methyl cellulose, and 2% w/w to 35% w/w enteric coating.

The cannabinoid oil may include CBD oil.

The method may further include any combination of the these features.

DETAILED DESCRIPTION OF EXAMPLE EMBODIMENTS

The cannabinoid composition described here may be used to treat many different human or animal ailments, but some examples are particularly advantageous for treating gastrointestinal disorder symptoms such as those associated with functional gastrointestinal disorders including irritable bowel syndrome ("IBS"), functional dyspepsia ("FD"), gastroparesis, diverticulosis and constipation; and those associated with inflammatory bowel diseases ("IBD"), including Crohn's disease, ileitis, and ulcerative colitis. Such examples of the composition are formulated to relieve symptoms of one or more of these problems by targeting the specific site of inflammation associated with the disorder.

Figure 1:
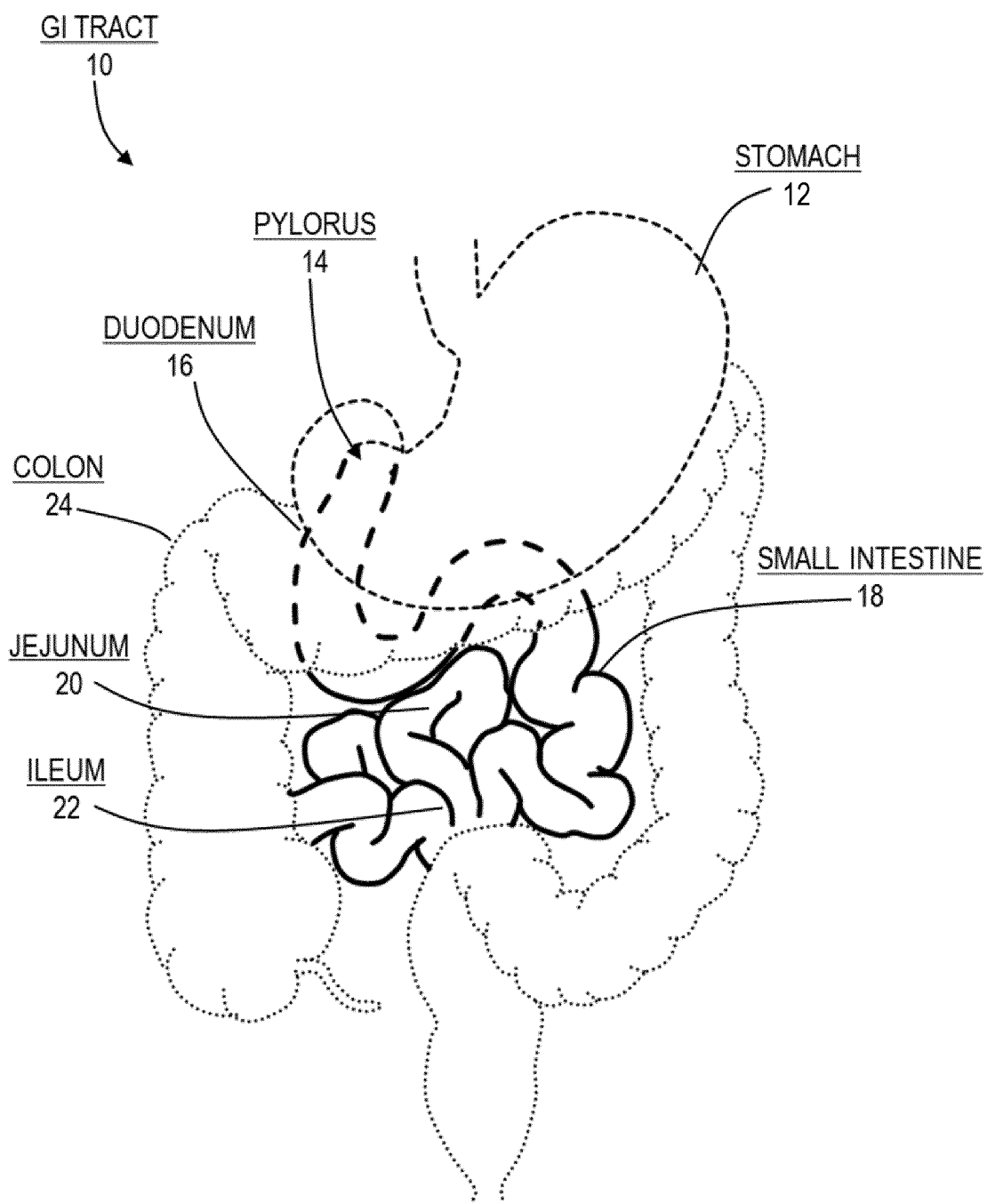
FIG. 1 is a schematic of a human's lower gastrointestinal tract, including the stomach, small intestine, and colon.

Pertinent parts of the gastrointestinal tract 10 are now generally described by referring to FIG. 1. When a subject ingests an oral dosage form, it travels to the stomach 12 where digestion takes place. If the dosage form is enteric coated, it will not release its contents into the stomach because the enteric coating will not dissolve at the stomach's pH, which is about 1 to 3.

From the stomach 12, the dosage form passes through the pylorus valve 14 into the duodenum 16, which is the upper (first) section of the small intestine 18. The pH in the duodenum 16 is about 4 to about 6. Once it leaves the duodenum 16, it enters the jejunum 20 where the pH is about 5.5 to about 6.5. After the jejunum 20, it enters the ileum 22 where the pH is about 6.5 to about 7.4. The cecum and colon 24, or large intestine, is past the ileum 22. The pH in the cecum drops down to about 5.7 but gradually increases to a pH of about 7. The pH of various sections of the GI tract are reported by Lalezari in *Annals of Gastroenterology*, Vol. 25, pgs. 1-5 (2012), by Evans, et al. in *Gut*, Vol. 29, pgs. 1035-41 (1988) and by Dressman, et al. in Pharmaceutical Research, Vol. 7(7), pgs. 756-761 (1990).

IBS symptoms originate in the jejunum according to Martinez, et al. in *Gut*, Vol. 62, pgs. 1160-68 (2013).

The duodenum is the site of inflammation for functional dyspepsia according to Micklefield, et al., *Phytotherapy Research*, Vol. 14, pgs. 20-23, (2000).

For Crohn's disease and ileitis, the inflammation is mostly localized in the ileum as reported by DiLauro et al. in *Curr. Gastroenterol. Rep.*, Vol. 12(4), pgs. 249-58 (2010).

Some examples of the composition are designed to minimize the food affect, which is the degree to which food enhances or inhibits the uptake of a cannabinoid in the body.

An example of composition includes a solid matrix including a cannabinoid oil and microcrystalline cellulose ("MCC"). The solid matrix is a combination of at least these two components in a solid form where the cannabinoid oil component has been taken up by the MCC and is stored within MCC's fibrous network. The solid matrix may be produced by a wet granulation process in which the cannabinoid oil and MCC are granulated together. The wet granulation process may be performed using a conventional pharmaceutical mechanical wet granulation technique such as high shear granulation, mortar and pestle, and fluidized bed granulation, among other possible examples.

Figure 2:
FIG. 2 is a photograph of a solid matrix formed from wet granulating MCC and CBD oil.

During the granulation process, the MCC forms a solid matrix with the cannabinoid oil. The MCC fiber network forms a porous scaffolding to which the cannabinoid oil binds. The resulting solid matrix from wet granulation is composed of solid micrometer and millimeter sized granules that are substantially dry or not oily in texture. By being substantially dry, the granules have a powder texture. An example of the solid matrix is shown in FIG. 2.

The fact that MCC and cannabinoid oil can be combined to form such a solid matrix is surprising. MCC is known to be a hydrophilic polymer that will absorb water, but, because cannabinoid oils are substantially water insoluble, one would not expect MCC to absorb the cannabinoid oil very well.

It is surprising that MCC can store a relatively large amount of cannabinoid oil. In certain examples, the ratio of MCC to cannabinoid oil is from 1:4 to 4:1 or 0.5:1 to 1.5:1. In a particular example, the cannabinoid oil to MCC ratio in the solid matrix is about 1:1. This unique and newly discovered property allows for high dose loading of the cannabinoid oil in the dosage form.

MCC is a conventional pharmaceutical excipient that is widely used as a disintegrant in solid oral dosage forms. In examples of the present composition, however, the MCC functions as a release-controlling polymer and provides for a sustained release of cannabinoid(s) from the cannabinoid oil. The MCC may gradually release cannabinoid oil into the gastrointestinal tract rather than quickly dumping the entire dose at one site. Accordingly, the MCC may help overcome effects of dose dumping.

The cannabinoid oil is composed of at least one cannabinoid dissolved in an oil carrier. In certain examples, the cannabinoid oil is prepared by dissolving a substantially pure cannabinoid in a pharmaceutically acceptable medium chain triglyceride oil such as vegetable oil, sesame oil, coconut oil, or the like. In other examples the cannabinoid oil is a plant extract obtained from a *cannabis* plant such as CBD oil, *cannabis* oil, hemp extract, hemp oil, or the like.

Because such plant extracts are commercially available, methods of making a plant extract cannabinoid oil are not described in detail.

There are many cannabinoid compounds that the cannabinoid oil may include, including one or more of tetrahydrocannabinol ("THC"), cannabidiol ("CBD"), tetrahydrocannabinolic acid ("THCA"), cannabidiolic acid ("CBDA"), cannabinol ("CBN"), cannabigerol ("CBG"), cannabichromene ("CBC"), cannabicyclol ("CBL"), cannabivarin ("CBV"), tetrahydrocannabivarin ("THCV"), cannabidivarin ("CBDV"), cannabichromevarin ("CBCV"), cannabigerovarin ("CBGV"), cannabigerol monomethyl ether ("CBGM"), cannabielsoin ("CBE"), and cannabicitran ("CBT").

If it is undesirable to produce a psychoactive effect in the subject being treated, cannabinoid oil predominant in CBD, CBG, and/or CBC may be used. In a particular example, CBD oil is used as the cannabinoid oil. The predominant cannabinoid in CBD oil is CBD, but CBD oil may also contain lesser amounts of one or more other cannabinoids.

Some examples of the solid matrix may further include a hydrogel forming polymer such as a cellulose-based, starch-based, and/or povidone-based material. It is to be understood that "cellulose-based," "starch-based" binders, and "povidone-based" binders includes cellulose, starch, and povidone derivatives. When mixed with water, these materials swells to form a hydrophilic hydrogel matrix. Examples of cellulose-based hydrogel-forming materials include methylcellulose based polymers, including, for example, methylcellulose and hydroxypropyl methylcellulose. Using a hydrogel forming polymer in the solid matrix may be useful to modulate the rate of release of cannabinoid(s) from the cannabinoid oil from the solid matrix in the gastrointestinal tract.

The solid matrix may be combined with pharmaceutical excipients to form orally ingestible solid pharmaceutical dosage forms such as powders, granules, pills (tablets, capsules, caplets), multiparticulates, and sachets. Such excipients may include pharmaceutically acceptable fillers, stabilizers, binders, surfactants, processing aids, and/or disintegrants. By way of example only, examples of materials for performing these functions are provided.

Examples of fillers include dibasic calcium phosphate, extragranular MCC outside the solid matrix, lactose, sucrose, and/or another pharmaceutically acceptable filler.

Examples of binders include cellulosic water soluble polymers such as methyl cellulose, starch, hydroxypropyl cellulose, gelatin, polyvinylpyrrolidone, polyethylene glycol, hydroxypropyl methylcellulose and/or another pharmaceutically acceptable binder. The binder, in such cases, is extragranular, meaning it is outside the solid matrix.

Processing aids include pharmaceutically acceptable processing aids for improving the flowability of the materials during processing. Examples of processing aids include colloidal silicon dioxide, talc, magnesium stearate, stearin, and/or another pharmaceutically acceptable processing aid.

Examples of disintegrants include, croscarmellose sodium, polyvinylpyrrolidone (crospovidone) sodium starch glycolate, and/or another pharmaceutically acceptable processing aid.

If the dosage form is a tablet or the like, the solid matrix may be combined with the desired excipients to form the tablet by using a conventional tableting technique such as compression, for example.

In certain examples the dosage form is an oral multiparticulate dosage form. In a multiparticulate dosage form there are a plurality of individual particulates that are preferably spheroidal in shape and are sized to fit through the pylorus valve irrespective of the gastric phase of digestion. The diameter of each particulate is preferably in the range of about 0.1 mm to about 3 mm, about 1 mm to about 2.5 mm, about 0.1 to about 2 mm, 0.5 mm to 1.5 mm, 0.5 mm to 1.7 mm, 1.8 mm to 2.1 mm, 1.8 mm to 3 mm, 0.5 mm to 2.1 mm, 0.5 mm to 3 mm, or less than about 2 mm. Particulates of this diameter pass through pylorus valve when it is relaxed, meaning they do not remain in the stomach as long as single-unit capsules. Typically, a significant number of particulates will have passed through the stomach within about thirty minutes after ingestion. Such a multiparticulate dosage form may help minimize the food affect.

An example of a method of making the composition includes wet granulating microcrystalline cellulose and a cannabinoid oil together forming a solid matrix in which the cannabinoid oil is bound in the MCC. The solid matrix is combined the solid matrix with at least one pharmaceutical excipient to form an oral pharmaceutical dosage form.

Relative to many types of conventional wet granulation, forming the sold matrix may sometimes require increased mechanical energy to get the cannabinoid oil to bind within the MCC fibrous network. In certain examples, the wet granulating step is performed in a high shear mixer at elevated temperature for a time sufficient to make the sold matrix have a substantially dry and non-oily texture. The elevated temperature may be just above room temperature or from 26 degrees C. to 50 degrees C., for example. The time may be 10 minutes to 20 minutes or about 15 minutes, for example.

The individual spheroidal particulates may be prepared by an extrusion spheronization process. A core may be prepared by wet granulating the solid matrix and core excipients into a wet mass, extruding the wet mass to form an extrudate, cutting the extrudate into a plurality of core pieces, and spheronizing the core pieces. The spheronized core pieces are then dried in a dryer such as a fluid bed dryer to remove most of the water. If desired, the dried spheronized cores are then sieved to separate cores of different sizes.

In some examples, the dosage form is formulated to substantially prevent releasing the cannabinoid(s) of the cannabinoid oil in the stomach by including an enteric coating. The enteric coating material may be chosen to dissolve at a specific pH within the gastrointestinal tract, approximately corresponding to the pH at the site of inflammation caused by the disorder being treated. Accordingly, if a subject has been diagnosed with a particular gastrointestinal disorder and the site of inflammation for that disorder is known, one may choose an enteric coating that dissolves within the pH range where the site of inflammation is located.

Table 1 lists examples of some commercially available enteric coating materials and the pH at which they dissolve. The list of possible enteric coating materials is not limited only to these. Examples of other enteric coating materials include, for example, other methacrylic acid copolymers, cellulose acetate phthalate, polyvinyl acetate phthalate, and ethyl cellulose/sodium alginate coatings such as NUTRATERIC® (Colorcon, Inc).

TABLE 1

Examples of Enteric Coating Materials

| Brand | Company | Generic Name | Dissolution pH |
|---|---|---|---|
| KOLLICOAT ® MAE 30DP | BASF Corp. | Methacrylic acid-ethyl acrylate copolymer | 5.5 and above |
| EUDRAGIT ® FS 30D | Evonik Industries AG | Methacrylic copolymer with carboxylic acid functional groups | 7 and above |
| EUDRAGIT ® S100 | Evonik Industries AG | Anionic copolymers based on methacrylic acid and methyl methacrylate. | 7 and above |
| AQOAT ® AS-HF | Shin Etsu Chemical Co., Ltd | Hypromellose acetate succinate | 6 and above |

Some examples of the dosage form delay releasing the cannabinoid(s) from the cannabinoid oil until the dosage form reaches the site of inflammation, but once the dosage form arrives there and the enteric coating dissolves, the MCC matrix sustains the release of cannabinoid(s) of the cannabinoid oil at the site of inflammation.

In certain examples, the individual particulates of the multiparticulate dosage form include 10% w/w to 50% w/w cannabinoid oil, 40% w/w to 75% w/w microcrystalline cellulose, 2% w/w to 10% w/w binder such as methylcellulose or the like, and 2% w/w to 35% w/w enteric coating.

The following cannabinoid release profiles are provided for illustration only. For treating IBS, the dosage form may release cannabinoid(s) from the dosage form for about 2.5 to about 3 hours. For treating functional dyspepsia and/or gastroparesis, the dosage form may release cannabinoid(s) from the dosage form for about 1.5 hours. For treating Crohn's disease, each the dosage form may release cannabinoid(s) from the dosage form for about 4.5 to about 5 hours. For treating ulcerative colitis or diverticulitis, the dosage form may release cannabinoid(s) from the cannabinoid oil from about 4 hours to about 72 hours.

The multiparticulate dosage form may also provide a sustained release of cannabinoid(s) from the cannabinoid oil because the particulates do not all reach the site of inflammation at the same time. This means that there will be a somewhat continuous flow of particulates to the site of inflammation as the individual particulates pass through the intestines and the content in the stomach gradually passes thru the pyloric valve and enters the small intestine. An estimated time it takes the particulates to pass through the small intestine is about 3 to about 6 hours, including about 1 hour to pass through the duodenum and about 1.5 hours to pass through the jejunum plus about 2 hours to pass through the ileum. After passing through the small intestine, the time it takes the particulates to pass through the large intestine (colon) is about 4 hours to about 72 hours.

For the multiparticulate dosage form, the enteric coating may be applied over each core. For a pill dosage form, the enteric coating may be applied over the pill. The enteric coating may be about 2% w/w to about 35% w/w of the dosage form or about 3.5% w/w to about 50% w/w of the dosage form.

A particular example of an enteric coating material is a methacrylic acid based material such as a methacrylic acid based co-polymer, including a methacrylic acid/ethylacrylate co-polymer, an example of which is KOLLICOAT® MAE 30 DP. These materials may be combined with other materials such as plasticizers for forming an enteric coating solution.

An example of an enteric coating solution may include about 5% w/w to about 35% w/w water, 0.5% w/w to about 5% w/w plasticizer, about 0.05% w/w to about 5% w/w anti-adherent, and about 2% w/w to about 35% w/w methacrylic acid copolymer. An example of a plasticizer is triethyl citrate and an example of an anti-adherent is PLASACRYL® T20 (Emerson Resources, Inc.). PLASACRYL® T20 is an emulsion of anti-tacking agent and plasticizer and contains water, glyceryl monostearate, triethyl citrate and polysorbate 80.

The enteric coating may be applied to the dosage form by any conventional enteric coating technique such as by spray coating, fluid bed coating, and the like.

Certain examples may include a subcoating over the core and between the core and enteric coating. The subcoating may be about 3.5% w/w to about 40% w/w of the individual enteric coated particulate. The subcoating may be made of a pharmaceutically acceptable coating forming material such as a gelatin, hydroxypropyl methylcellulose or the like. The subcoating may be applied to the dosage form by any conventional pharmaceutical coating technique such as by spray coating, fluid bed coating, and the like.

The composition may be used to treat many different types of gastrointestinal disorders by providing relief from inflammation. The formulation can vary depending on the type of gastrointestinal disorder being treated.

The cannabinoid release profile in the body can be varied to treat different gastrointestinal disorders by formulating it to release the cannabinoid(s) of the cannabinoid oil at the site of inflammation in gastrointestinal tract associated with the disorder being treated. This is accomplished by selecting an enteric coating that dissolves at about the pH of the site of inflammation and by controlling the release rate of cannabinoid(s) from the cannabinoid oil at the site of inflammation using different particulate diameters and/or a disintegrant.

To treat gastrointestinal disorder symptoms associated with inflammation of the jejunum, such as irritable bowel syndrome, the composition may be formulated to minimize the amount of cannabinoid(s) released into the stomach and colon, so that most of, or at least about 50% to about 75% of, the cannabinoid(s) is released in the small intestine, particularly the jejunum. Preferably, 20% or less of the cannabinoid(s) is released into the stomach and 20% or less of the cannabinoid(s) is released into the colon. Also, the cannabinoid(s) is preferably gradually released over the course of about 2 to about 4 hours after the dosage form passes the pylorus valve in order to deliver the cannabinoid(s) locally in the jejunum. This release profile treats IBS by treating gastrointestinal symptoms associated with IBS. In such a composition, the average diameter of the particulates may, for example, be 0.5 mm to 1.7 mm.

To treat gastrointestinal disorders associated with inflammation of the duodenum, such as functional dyspepsia and/or gastroparesis, the dosage form is formulated so that the cannabinoid(s) is substantially released in the duodenum after the dosage form passes through the stomach and pylorus valve over the course of about 0 to about 2 hours. This delivers the cannabinoid(s) locally to the duodenum to substantially relieve the symptoms associated with functional dyspepsia and gastroparesis, for example. Preferably, 20% or less of the cannabinoid(s) is released in the stomach and 20% or less of the cannabinoid(s) is released in the later sections of the intestines, including the ileum, and colon. To obtain an effective release of cannabinoid(s) from the cannabinoid oil into the duodenum, the dosage form may include a disintegrant. The amount of disintegrant, if used, may be about 1% w/w to 20% w/w of the dosage form. Use of a disintegrant is not necessary in every example. In such a composition, the average diameter of the particulates may, for example, be 0.5 to 1.7 mm.

To treat gastrointestinal disorders associated with inflammation of the ileum; such as inflammatory bowel diseases, including Crohn's disease, ileitis, and/or ulcerative colitis; the dosage form is formulated so that the cannabinoid(s) is substantially released in the ileum after the dosage form passes through the stomach and pylorus valve over the course of about 4 to about 6 hours. This delivers the cannabinoid(s) locally to the ileum to substantially relieve the symptoms associated with such disorders. Preferably, 50% to 75% of the cannabinoid(s) is released in the ileum. Preferably, greater than 70% of the cannabinoid(s) is released after the particulates reach the pH of the ileum. To obtain an effective release of cannabinoid(s) from the cannabinoid oil into the ileum. In such a composition, the average diameter of the particulates may, for example, be 0.5 to 1.7 mm.

In some cases it may be desirable to administer a dosage form that can continuously release the cannabinoid(s) more generally throughout the intestines to treat less acute inflammations. This may be achieved using particulates having an average diameter of about 1.8 to 3 mm. The larger average diameter ensures a slower and more sustained release of cannabinoid(s) for at least 5 to 8 hours after administration.

A general method of treatment includes orally administering an effective amount of the pharmaceutical dosage form to a subject having a gastrointestinal disorder. The dosage form may include any of the features described above. Examples of gastrointestinal disorders include, but are not limited to inflammation of the duodenum, inflammation of the jejunum, inflammation of the ileum, IBS, FD, gastroparesis, Crohn's disease, ulcerative colitis, ileitis, and constipation.

An exemplary method of treating inflammation of the jejunum, which may be caused by irritable bowel syndrome, includes orally administering an effective amount of the pharmaceutical dosage form to a subject having the inflammation of the jejunum. The dosage form may include any of the features described above. The dosage form releases most of the cannabinoid(s) in the subject's jejunum. In some examples, the dosage form releases at least about 50% to about 75% of the cannabinoid(s) into the jejunum.

An exemplary method of treating inflammation of the duodenum, which may be caused by functional dyspepsia and/or gastroparesis, includes orally administering an effective amount of the dosage form to a subject having the inflammation of the duodenum. The dosage form may include any of the features described above. The dosage form may release most of the cannabinoid(s) in the subject's duodenum. In some examples, the dosage form releases at least about 50% to about 75% of the cannabinoid(s) into the duodenum.

An exemplary method of treating inflammation of the ileum, which may be caused by an inflammatory bowel disease such as Crohn's disease, ulcerative colitis, and ileitis; includes orally administering an effective amount of the dosage form to a subject having the inflammation of the ileum. The dosage form may include any of the features described above. The dosage form may release most of the cannabinoid(s) in the subject's ileum. In some examples, the dosage form releases at least about 50% to about 75% of the cannabinoid(s) into the ileum.

"Relief" that subjects obtain from the dosage form is a measurable quantity, not just a subjective determination, because relief from gastrointestinal disorder symptoms may be quantified statistically using conventional clinical protocols from a pool of subjects. These clinical protocols may include the use of the Gastrointestinal Symptom Rating Scale (GSRS) or the Visual Analog Scale (VAS). Both of these scales quantify a particular subject's symptoms based on the subject's responses to various questions pertaining to those symptoms. By recording GSRS and/or VAS data for a pool of subjects at various stages of treatment with the treatment composition, one can statistically measure how quickly the treatment composition relieves the subject's symptoms. An example of a suitable protocol for measuring "relief" using the VAS is reported by Hawker, et al. in *Arthritis Care & Research*, Vol. 63 No. S11, pgs. S240-S252 (2011).

The dosage form includes an effective amount of the cannabinoid oil. An effective amount is an amount that is sufficient to affect a disease or condition in the body. An effective amount of cannabinoid oil may be, for example: 0.01-5,000 mg, 0.01-1,000 mg, 0.01-500 mg, 0.01-200 mg, 0.01-100 mg, 0.01 to 50 mg, 0.01-25 mg, 0.01-10 mg, or 0.01-5 mg. The effective amount can vary outside of these ranges as well. The weight in mg is often calibrated to the body weight of the subject in kg, thus these example doses may also be written in terms of mg/kg of body weight per day.

In practice, the effective amount may vary depending on numerous factors associated with the subject, including age, weight, height, severity of the condition, administration technique, and other factors. The effective amount administered to a subject may be determined by medical personnel taking into account the relevant circumstances.

The effective amount may be determined or predicted from empirical evidence. Specific dosages may vary according to numerous factors and may be initially determined on the basis of experimentation.

The dosage form may be administered as a single dose or as part of a dosage regimen. For a dosage regimen, the therapeutically effective amount is adjustable dose to dose to provide a desired therapeutic response.

Multiple doses may be administered at a predetermined time interval and subsequent doses may be proportionally reduced or increased, depending on the situation.

The dosage form may be administered sporadically when needed for treating inflammations of the gastrointestinal tract or may be administered as part of a long term regimen for treating gastrointestinal disorders. A treatment subject may be a human or animal.

It should be understood that where this disclosure makes reference to treating a gastrointestinal disorder, that the terms "treat," "treating," or any other variation of the word "treat" include prevention of, management of, and substantial symptom relief from the gastrointestinal disorder.

EXAMPLES

The following examples are provided to illustrate aspects of certain examples of the composition. The scope of possible examples is not limited to the details of these examples.

Example 1: Wet Granulation of MCC and CBD Oil

A solid matrix of MCC and CBD oil was prepared by mechanically wet granulating about 2 mL of CBD oil with about 2 grams of MCC (MCC 102) for two minutes. The CBD oil was manufactured by SUNMED ORGANIC INGREDIENTS™ and contained organic medium chain triglyceride oil, hemp extract, organic flavoring, and plant-derived terpenes, with 500+ mg of total cannabinoids (CBD, CBG, CBC, CBN and CBD-V). The resulting wet granulation had a substantially dry powder appearance and did not have an oily texture. This proves that CBD oil is capable of being bound in an MCC scaffolding even though MCC is a hydrophilic polymer. FIG. 2 is a photograph of the wet granulation.

Example 2: Preparation of an Example Formulation

Spheroidal cores are prepared by blending 50 kg of microcrystalline cellulose, 5 kg methyl cellulose, and 50 kg CBD oil with water to form a wet mass. The wet mass is granulated in a high shear granulator then extruded and spheronized. The spheronized wet cores are dried in a fluid bed dryer to form uncoated dried cores. The drying temperature is about 16 degrees C. The diameter of the uncoated dried cores is set by selecting by cutting the extrudate into appropriate size pieces prior to spheronization.

An enteric coating is applied to the uncoated dried cores using 31 kg of a 20% w/w solution of KOLLICOAT® MAE 30 DP, PLASACRYL® T20, triethyl citrate, and water. The dry solids weight of KOLLICOAT® MAE 30 DP is about 5 kg. The dry solids weight of triethyl citrate is about 0.3 kg. The dry solids weight of PLASACRYL® T20 is about 0.5 kg. The enteric coated cores are dried at about 40 degrees C. The enteric coating provides a weight gain to the cores of about 10% w/w.

If desired, the uncoated dried cores may optionally be subcoated with 37 kg of a subcoating solution containing about 15% acid bone gelatin and 85% USP water and dried. The subcoating provides a weight gain to the cores of about 10% w/w.

If desired, an optional finish coat may be applied over the enteric coat. The finish coat is 26 kg of a finish coat solution containing about 10% w/w hydroxypropyl methylcellulose and 90% water. The finish coated particulates are dried at about 40 degrees C. The finish coat provides a weight gain to the enteric coated cores of about 2% w/w.

The finished particulates are loaded into gelatin capsules of the desired size.

Example 3: Example Formulations

In a composition that may be useful for treating inflammation of the jejunum, a capsule of the multiparticulates includes 200 mg CBD oil, 200 mg MCC, 20 mg methyl cellulose (binder), 20 mg gelatin (subcoat), 22 mg enteric coat. The particulate diameter is about 1.5 mm In a composition that may be useful for treating inflammation of the duodenum, a capsule of the multiparticulate includes 200 mg CBD oil, 200 mg MCC, 20 mg methyl cellulose, 50 mg croscarmellose sodium (disintegrant), 20 mg gelatin (subcoat), and 22 mg enteric coat. The particulate diameter is about 1.5 mm.

In a composition that may be useful for treating inflammation of the ileum includes, a capsule of the multiparticulates includes 200 mg CBD oil, 200 mg MCC, 20 mg methyl cellulose (binder), 20 mg gelatin (subcoat), 22 mg enteric coat. The particulate diameter is about 1.5 mm.

In a sustained release composition for releasing the cannabinoid(s) throughout the intestines, a capsule of the multiparticulates includes 200 mg CBD oil, 200 mg MCC, 20 mg methyl cellulose (binder), 20 mg gelatin (subcoat), 22 mg enteric coat The particulate diameter is about 2 mm.

This disclosure describes exemplary embodiments, but not all possible embodiments of the compositions and methods. Where a particular feature is disclosed in the context of a particular example, that feature can also be used, to the extent possible, in combination with and/or in the context of other examples. The compositions and methods may be embodied in many different forms and should not be construed as limited to only the examples described here.

The compositions and methods are not limited to the details described in connection with the example embodiments. There are numerous variations and modification of the compositions and methods that may be made without departing from the scope of what is claimed.

That which is claimed is:

1. A method for preparing an oral pharmaceutical dosage form, the method comprising:
   wet granulating microcrystalline cellulose and a cannabinoid oil together forming a solid matrix in which the cannabinoid oil is bound in the microcrystalline cellulose; and
   combining the solid matrix with at least one pharmaceutical excipient to form the oral pharmaceutical dosage form,
   the oral pharmaceutical dosage form comprising a plurality of individual particulates, wherein the individual particulates are spheroidal and comprise:
   (a) a solid core including an effective amount of the cannabinoid oil bound in the microcrystalline cellulose (MCC) in a ratio of the cannabinoid oil to the MCC of 0.5:1 to 1.5:1; and
   (b) an enteric coating over the solid core,
   wherein the individual particulates are selected from the group consisting of:
   (i) the individual particulates have an average diameter of 0.5 mm to 1.7 mm and further comprise an enteric coating material and a disintegrant combination configured for the individual particulates to release at least about 50% of the cannabinoid oil in a subject's duodenum for treating inflammation of the duodenum;
   (ii) the individual particulates have an average diameter of 0.5 to 1.7 mm and are configured to release at least about 50% of the cannabinoid oil in a subject's jejunum for treating inflammation of the jejunum; and
   (iii) the individual particulates have an average diameter of 0.5 to 1.7 mm and are configured to release at least about 50% of the cannabinoid oil in a subject's ileum for treating inflammation of the ileum,
   wherein the individual particulates comprise 10% w/w to 50% w/w of the cannabinoid oil, 40% w/w to 75% w/w of the microcrystalline cellulose, 2% w/w to 10% w/w methyl cellulose, and 2% w/w to 35% w/w of the enteric coating.

2. The method of claim 1, wherein the wet granulating is performed in a high shear mixer above room temperature for 10 minutes to 20 minutes.

3. The method of claim 1, wherein the cannabinoid oil is bound in microcrystalline cellulose by being stored within microcrystalline cellulose's fibrous network.

4. The method of claim 1, wherein the cannabinoid oil bound in microcrystalline cellulose is substantially dry.

5. The method of claim 1, wherein the cannabinoid oil includes CBD oil.

6. The method of claim 1, wherein the individual particulates have the average diameter of 0.5 mm to 1.7 mm, and further comprise the enteric coating material and the disintegrant combination that cause the individual particulates to release at least about 50% of the cannabinoid oil in a subject's duodenum for treating inflammation of the duodenum.

7. The method of claim 1, wherein the individual particulates have the average diameter of 0.5 to 1.7 mm, and are configured to release at least about 50% of the cannabinoid oil in the jejunum for treating inflammation of the jejunum.

8. The method of claim 1, wherein the individual particulates have an average diameter of 0.5 to 1.7 mm, and are configured to release at least about 50% of the cannabinoid oil in an ileum for treating inflammation of the ileum.

9. The method of claim 6, wherein the enteric coating dissolves at a pH between 4 and 6.

10. The method of claim 7, wherein the enteric coating dissolves at a pH between 5.5 and 6.5.

11. The method of claim 8, wherein the enteric coating dissolves at a pH between 6.5 and 7.4.

12. The method of claim 9, wherein the enteric coating is methacrylic acid-ethyl acrylate copolymer.

13. The method of claim 10, wherein the enteric coating is hypromellose acetate succinate.

14. The method of claim 11, wherein the enteric coating is methacrylic copolymer with carboxylic acid functional groups.

15. The method of claim 1, wherein the individual particulates further comprise a subcoating between the solid core and the enteric coating.

16. The method of claim 15, wherein the subcoating is gelatin.

17. The method of claim 1, wherein the solid matrix further comprises a hydrogel forming polymer.

* * * * *